US012629295B2

(12) United States Patent

O'Connor et al.

(10) Patent No.: US 12,629,295 B2

(45) Date of Patent: May 19, 2026

(54) FOUR-DIMENSIONAL ANALYSIS SYSTEM, APPARATUS, AND METHOD

(71) Applicant: Edgewell Personal Care Brands, LLC, Chesterfield, MO (US)

(72) Inventors: Alexander O'Connor, Cincinnati, OH (US); Richard Timmers, Saddle Brook, NJ (US)

(73) Assignee: Edgewell Personal Care Brands, LLC, Chesterfield, MO (US)

( * ) Notice: Subject to any disclaimer, the term of this patent is extended or adjusted under 35 U.S.C. 154(b) by 187 days.

(21) Appl. No.: 18/485,676

(22) Filed: Oct. 12, 2023

(65) Prior Publication Data

US 2024/0033142 A1 Feb. 1, 2024

Related U.S. Application Data

(63) Continuation of application No. 17/161,969, filed on Jan. 29, 2021, now abandoned, which is a continuation of application No. 16/227,090, filed on Dec. 20, 2018, now Pat. No. 10,940,058, which is a continuation of application No. 15/354,412, filed on Nov. 17, 2016, now Pat. No. 10,201,463.

(60) Provisional application No. 62/256,405, filed on Nov. 17, 2015.

(51) Int. Cl.
*A61F 13/84* (2006.01)
*G01N 23/046* (2018.01)

(52) U.S. Cl.
CPC ........... *A61F 13/84* (2013.01); *G01N 23/046* (2013.01); *A61F 2013/8488* (2013.01)

(58) Field of Classification Search
None
See application file for complete search history.

(56) References Cited

U.S. PATENT DOCUMENTS

| | | |
|---|---|---|
| 4,148,317 A | 4/1979 | Loyer |
| 4,729,246 A | 3/1988 | Melgaard et al. |
| 4,846,802 A | 7/1989 | Sanders, III |
| 5,307,018 A | 4/1994 | Gadgil |
| 6,604,436 B1 | 8/2003 | Lewandowski et al. |

(Continued)

FOREIGN PATENT DOCUMENTS

| | | |
|---|---|---|
| EP | 0278601 A | 8/1988 |
| JP | 2008500887 A | 1/2008 |

(Continued)

OTHER PUBLICATIONS

Unofficial English translation of Japanese Office Action issued in connection with corresponding JP Application No. 2018-524746 dated Dec. 9, 2019.

(Continued)

*Primary Examiner* — Daniel S Larkin

(74) *Attorney, Agent, or Firm* — BUCHANAN INGERSOLL & ROONEY PC

(57) ABSTRACT

A system for measuring fluid absorption and retention properties of various samples having one or more materials, layers and/or articles. The system includes an optically or radiographically transparent fixture. The system enables measuring voxels having a grayscale value that demonstrate a difference in fluid densities and thereby enable the study of fluid flow and movement within and/or amongst various materials and articles in real time.

7 Claims, 16 Drawing Sheets

(56)     References Cited

U.S. PATENT DOCUMENTS

| | | |
|---|---|---|
| 6,710,221 B1 | 3/2004 | Pierce et al. |
| 7,389,705 B2 | 6/2008 | Omairi et al. |
| 8,166,834 B2 | 5/2012 | Dougherty et al. |
| 10,052,819 B2 | 8/2018 | Wu |
| 2002/0128623 A1 | 9/2002 | Kehoe |
| 2005/0145048 A1 | 7/2005 | Moir et al. |
| 2005/0273036 A1 | 12/2005 | Osborn, III et al. |
| 2006/0069369 A1 | 3/2006 | Feldkemp et al. |
| 2006/0247599 A1 | 11/2006 | Mullen et al. |
| 2010/0005911 A1 | 1/2010 | Scott et al. |
| 2010/0274209 A1 | 10/2010 | Roe et al. |
| 2011/0190720 A1 | 8/2011 | Skreosen |
| 2011/0200976 A1* | 8/2011 | Hou ...................... G09B 23/32 |
| | | 434/267 |
| 2012/0321040 A1 | 12/2012 | Maltbie et al. |
| 2014/0102183 A1 | 4/2014 | Agami et al. |
| 2015/0185172 A1 | 7/2015 | Kisela et al. |
| 2017/0135876 A1 | 5/2017 | O'Connor et al. |
| 2019/0142656 A1 | 5/2019 | O'Connor et al. |

FOREIGN PATENT DOCUMENTS

| | | |
|---|---|---|
| JP | 2008501433 A | 1/2008 |
| JP | 2013072734 A | 4/2013 |
| JP | 2013164277 A | 8/2013 |

OTHER PUBLICATIONS

Edana, "Tampons absorbency 350.0-02 Syngina method", Feb. 1, 2002, pp. 215-221, URL: http://www.ahpma.co.uk/docs/EDANA_Syngina2.pdf, XP055349937.

International Preliminary Report on Patentability issued for PCT Application No. PCT/US2016/062495 dated May 22, 2018.

International Search Report and Written Opinion issued for PCT Application No. PCT/US2016/062495 dated Mar. 8, 2017.

Hou, Mari et al. "Understanding the tampon density and density gradient through computed tomography imaging", Textile Research Journal, Apr. 1, 2016, vol. 86 issue: 6, pp. 573-579.

* cited by examiner

FOUR-DIMENSIONAL ANALYSIS SYSTEM, APPARATUS, AND METHOD

CROSS-REFERENCE TO RELATED APPLICATIONS

This application is a continuation of U.S. patent application Ser. No. 17/161,969, filed Jan. 29, 2021, now abandoned, which is a continuation application of U.S. patent application Ser. No. 16/227,090, filed Dec. 20, 2018, now U.S. Pat. No. 10,940,058, issued on Mar. 9, 2021, which is a continuation application of U.S. patent application Ser. No. 15/354,412, filed Nov. 17, 2016, now U.S. Pat. No. 10,201,463, issued on Feb. 12, 2019, which claims the benefit of priority to U.S. Provisional Patent Application Ser. No. 62/256,405 filed on Nov. 17, 2015, the contents of which are incorporated by reference herein.

BACKGROUND

Studies and research have been undertaken to determine the efficacy of personal care products. For example, in the context of feminine hygiene products, research has been performed to determine the effectiveness of the products in absorbing fluid.

The quality of the results that are obtained in connection with the research are influenced by the quality of the test system, apparatus, and methodology that are used. For example, due to the complexity of the imaging technology (e.g., computed tomography (CT) scanning) that is used as well as variations in the products/samples that are being analyzed, it is difficult to determine a grayscale value that best represent those volumetric pixels (voxels) of reconstructed data sets that correspond to fluid entering a given sample. In the context of medical imaging, CT scans can be low resolution and fail to recreate real-time conditions despite successive scans or a series of scans. Further still, in vivo set-ups can be costly and require significant amounts of time to, inter alia, organizing subject populations, creating a test protocol, scheduling the scans and analyzing the results. Accordingly, there is uncertainty that is introduced that is difficult, if not impossible, to account for. Furthermore, due to delays between the capturing of the image and when the associated data set becomes available, events such as an advancement of a fluid-front in association with the sample may be missed or unaccounted for.

SUMMARY OF THE PRESENT DISCLOSURE

The present disclosure provides a system for determining real-time fluid dynamics within or near a device. The system includes a fixture that simulates an in vivo set-up via at least one characteristic. The fixture simulates bodily pressure exerted against a device. The device is a consumer product, such as a hygiene device, an implement, and/or a medical device. The device is an internally worn device or an externally worn (or externally manipulated) device. In some embodiments, the device is dynamic in that it changes in shape, configuration and/or other mechanical properties upon implementation (i.e., upon contacting the body, fluid and/or by its design). In some embodiments, the device is dynamic due to other forces exerted upon it. Such forces could be bodily, such as pressure exerted by the body cavity against an internally worn device. Such forces could be from other objects, such as garments worn adjacent the body, pressure exerted by a bed or a chair when a person is lying or sitting, and/or limbs directing the device's movement and/or affecting the device's configuration.

The fixture is a somewhat simple structure as exemplified in FIGS. 1-4. The fixture accommodates a device (herein referred to as the "sample" or "test sample").

The fixture is a more complex structure as shown in FIGS. 5-7. Such fixtures include multiple regions that can be fixed and thus relative movement amongst these regions is limited, or these regions can be separate, attachable and/or movable with respect to each other to create a dynamic in vivo-esque profile.

The fixture is a further refined structure as shown in FIGS. 8A-8C. Such fixtures are formed from human body scans or measurements, both internal and external. Such fixtures are static and/or dynamic (i.e., the one or more leg regions are able to move with respect to the torso or pelvic region).

The fixture is radiographically transparent or translucent ("radiotransparent") such that a scanning means (such as CT or micro-CT) can be employed. Optionally, the fixture is visually transparent. The fixture is attached to a platform that permits rotation about at least one axis, thereby permitting imaging of the sample in real time. The fixture can move about multiple axes to generate different views and/or different configurations to replicate the position and functionality of the sample of the device in simulated conditions. Movement of a fixture in at least one direction, plane and/or along an axis other than to generate an image, can be done with a cadence that simulates in vivo interaction and motion amongst body parts and the device.

BRIEF DESCRIPTION OF THE DRAWINGS

The present disclosure is illustrated by way of example and not limited in the accompanying figures in which like reference numerals indicate similar elements.

DETAILED DESCRIPTION

Figure 1:
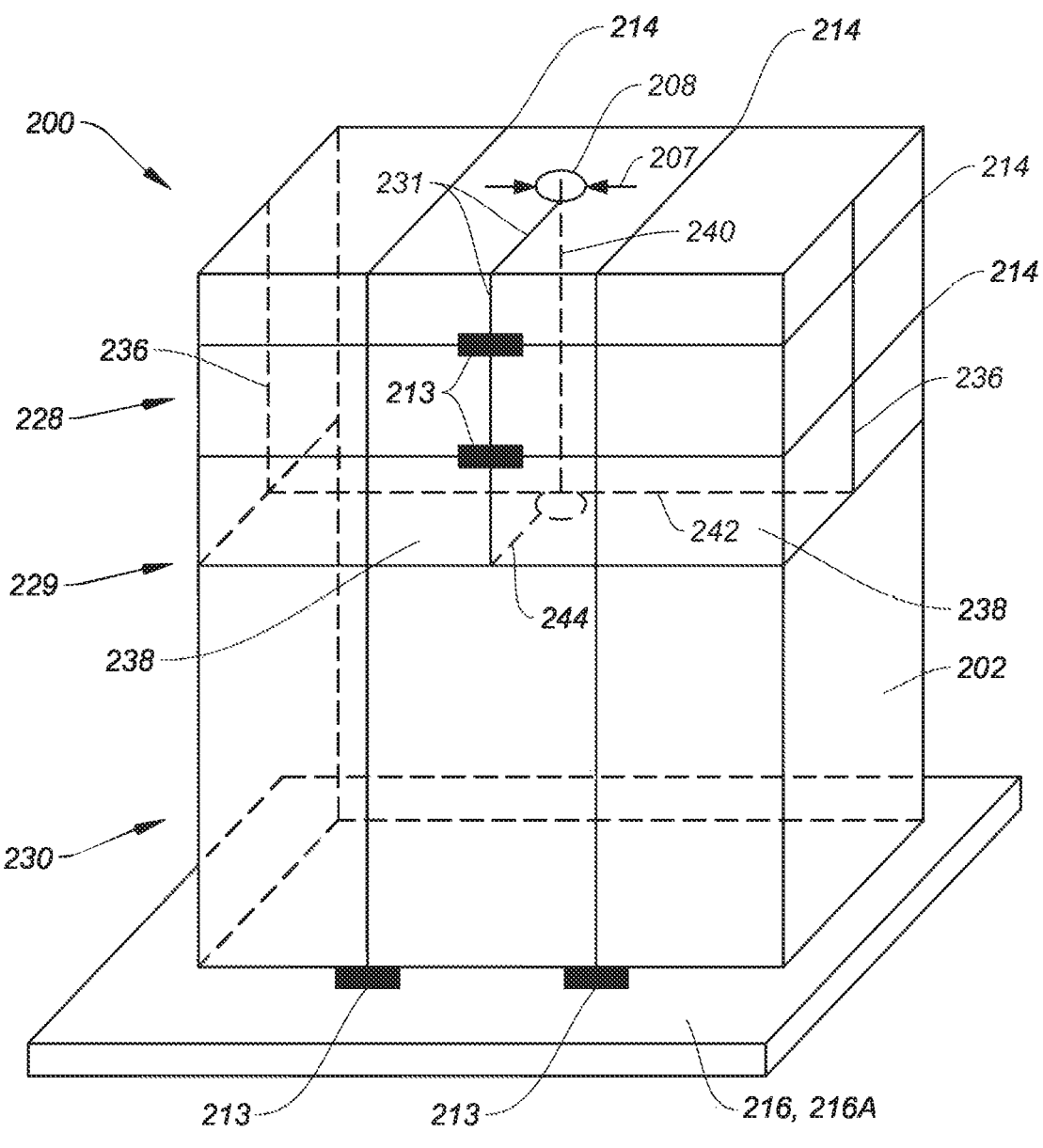
FIG. 1 illustrates a diagrammatic representation of one embodiment of the present disclosure's test fixture apparatus.
Figure 2:
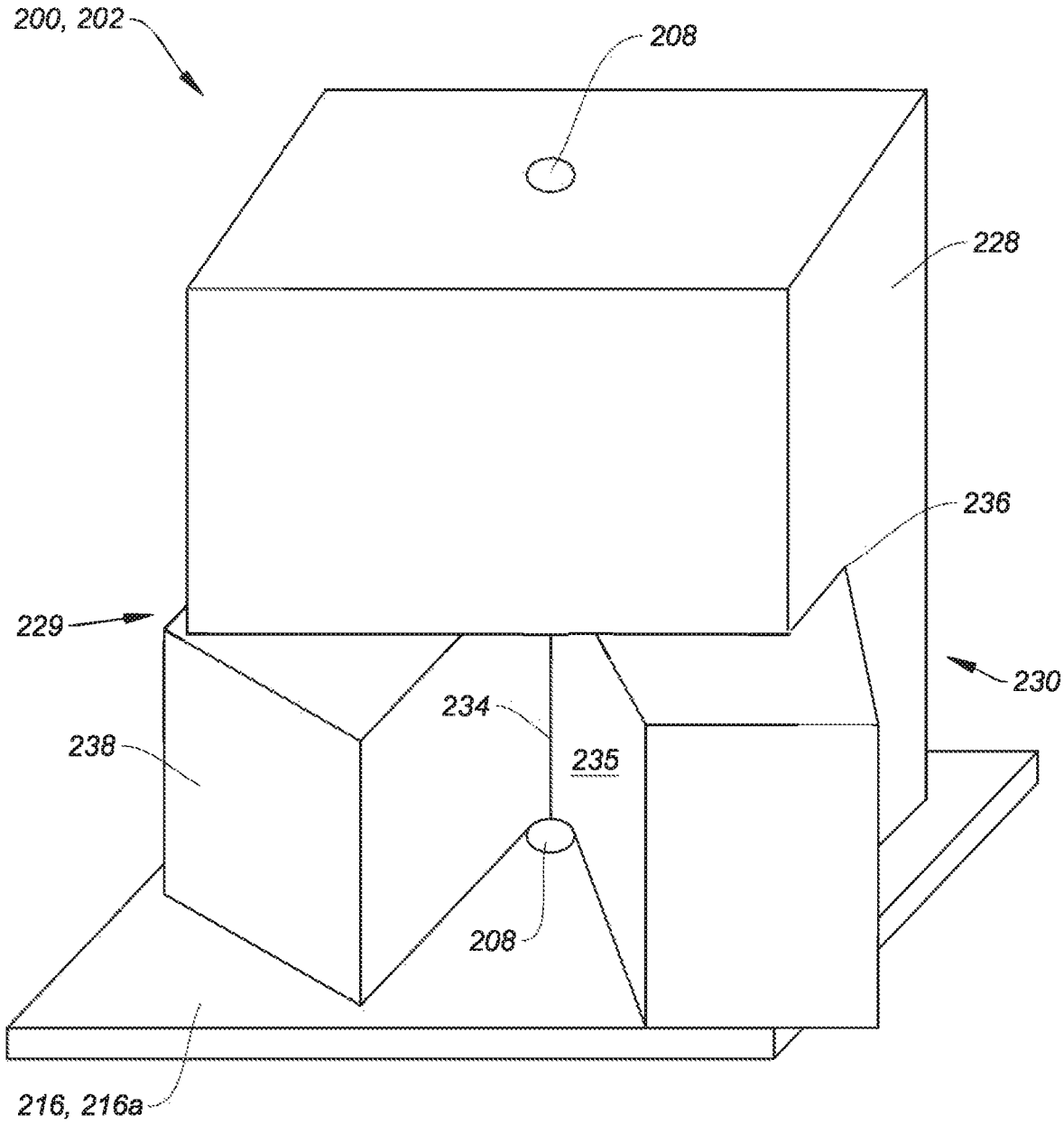
FIG. 2 illustrates a diagrammatic representation of one embodiment of the present disclosure's test fixture apparatus.

It is noted that various connections are set forth between elements in the following description and in the drawings (the contents of which are included in this disclosure by way of reference). It is noted that these connections are general and, unless specified otherwise, may be direct or indirect and that this specification is not intended to be limiting in this respect. A coupling between two or more entities may refer to a direct connection or an indirect connection. An indirect connection may incorporate one or more intervening entities.

Aspects of the disclosure are directed to systems, apparatuses, and methods for performing an analysis on one more samples. A sample 204 may be associated with a device, such as a personal care product, including hygiene products, medical devices, including diapers and feminine hygiene products worn internally and/or externally (e.g., a pledget, an applicator, a menstrual cup, a napkin, a pad, a liner, a pessary, a suppository etc.) for menstrual and/or incontinence purposes. As for suppositories, the disclosure demonstrates the dissolution and/or transition of a suppository as it enters the body and chemically interacts with the body, thereby inducing a change in the suppository's state or transport of the material contained within or delivered by the suppository. In some embodiments, a fluid may be injected/introduced to the sample 204, and an analysis may be performed to determine/characterize how the fluid flows in/through the sample 204. For example, if a flow rate of fluid 246 introduced to the sample 204 is a constant, a grayscale value that best represents volumetric pixels (voxels) of a reconstructed data set that correspond to the fluid 246 entering the sample 204 can be determined heuristically. As one skilled in the art would appreciate, a grayscale value may serve as a representation of an intensity, ranging from black to white, of a voxel. A voxel may be associated with a three-dimensional data structure defined by a grayscale value, a length, a width, a height, and a relative position in space.

Referring now to FIG. 1, a fixture 202 is shown. The fixture 202, as at least a part of system 200, may be used to represent/simulate a fluid flow associated with one or more samples 204.

The fixture 202 may be configured to retain a sample 204 (e.g., a personal care product) that is to be subjected to an analysis in accordance with aspects of the disclosure. The retention of the sample 204 may be facilitated by the fixture 202 and/or use of retaining mechanism 206. The retaining mechanism 206 may be made of foam or other material, such as materials similar to garments, underwear and/or beds, chairs, etc. The retaining mechanism 206 may also have a hydrophobic layer or portion, such as a plastic, film or silicone. The retaining mechanism 206 may exhibit properties, such as pressure, that simulate properties of tissues such that the in vitro set-up mimics an in vivo set-up. The retaining mechanism 206 may include a bore 208 for holding the sample 204 that is in communication with a fluid line 211, particularly the fluid line end 211a. In some embodiments, fixture 202 is also a retaining mechanism 206. Bore 208 may be generally cylindrical and/or have an arcuate or varying geometry. In some embodiments, fixture 202 has a recess 208a that further assists in retaining sample 204. Recess 208a is in concert with bore 208 and creates a slightly raised lip such that sample 204 can be more easily positioned within or adjacent to fixture 202. Bore 208 can be positioned in varying configurations and/or orientations within fixture 202 such that fluid flow can enter or surround sample 204 as per known gravitational forces.

Figure 3:
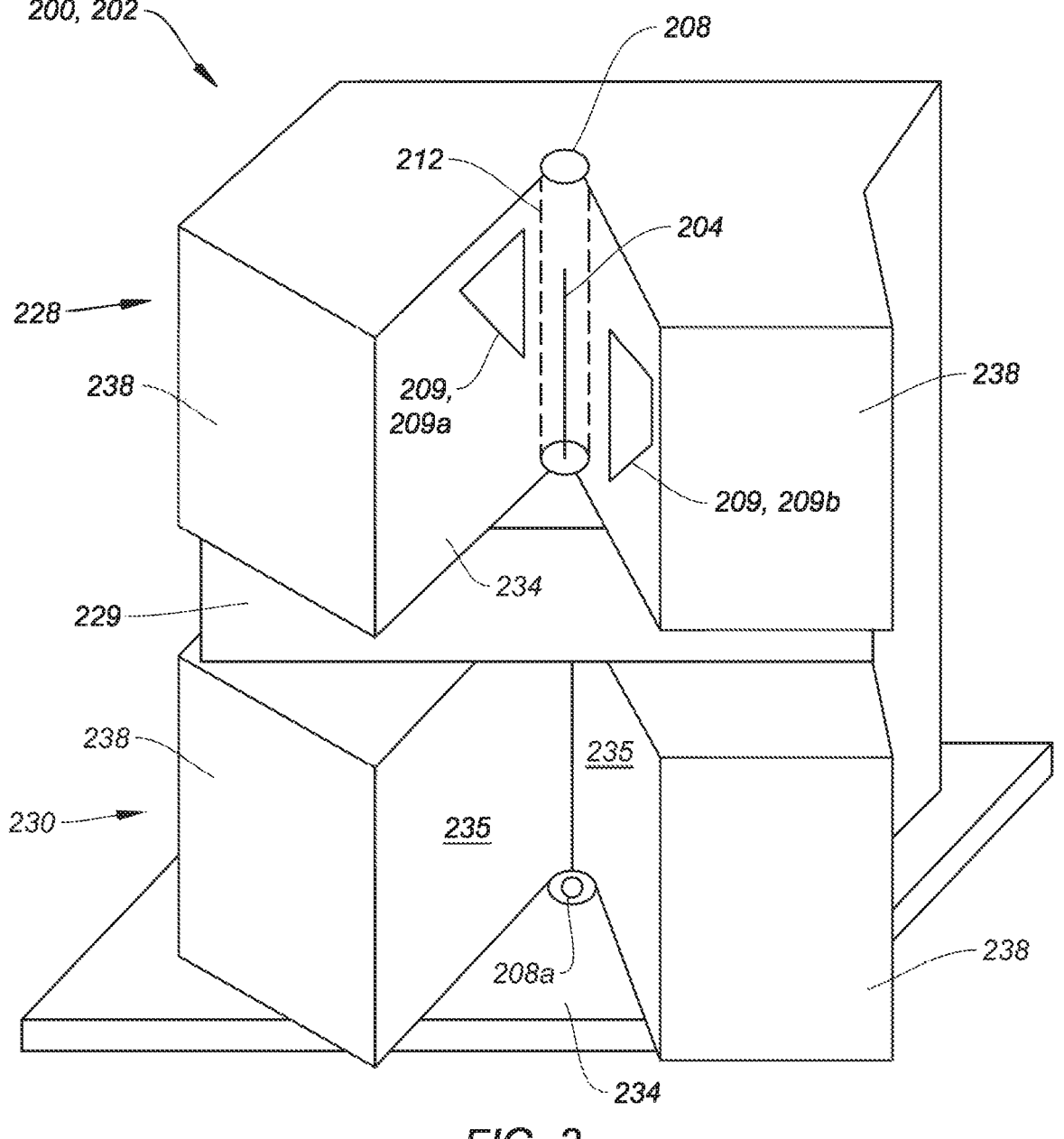
FIG. 3 illustrates a diagrammatic representation of one embodiment of the present disclosure's test fixture apparatus.
Figure 4:
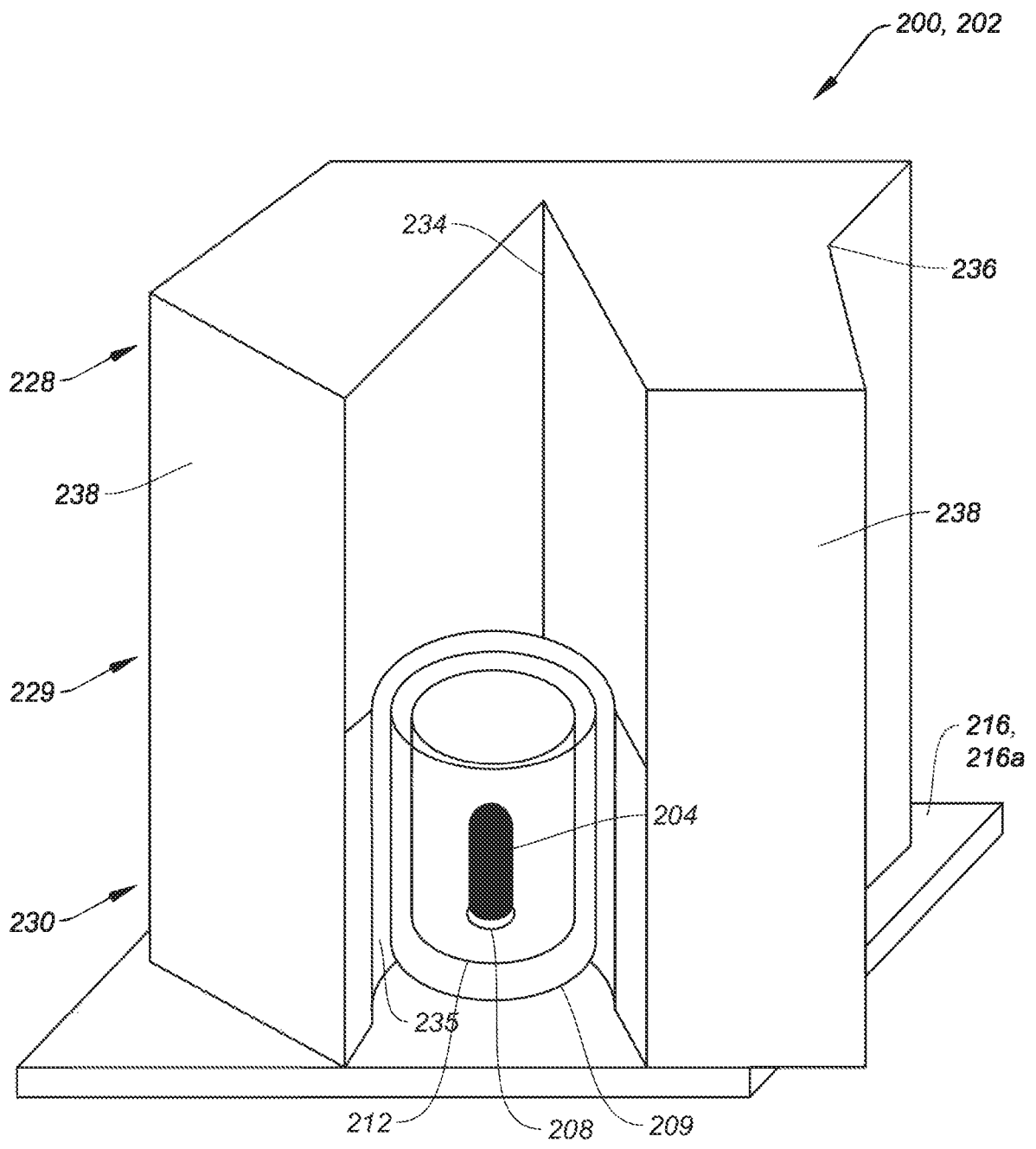
FIG. 4 illustrates a diagrammatic representation of one embodiment of the present disclosure's test fixture apparatus.

Fixture 202 has an upper region 228 and a lower region 230, and as shown more easily in FIG. 3, a middle region 229. As shown in FIGS. 1-4, the upper, lower and middle regions can have a variety of configurations and purposes, depending on the set-up and predetermined goals of the study. Fixture 202 has a bore 208 and an opening 231. Bore 208 provides access for sample 204 and/or a line 211 transmitting fluid into, around or proximal to the sample 204. Opening 231 permits further access to the interior volume 234 of fixture 202, permitting easier insertion and/or removal of sample 204 and other items described throughout the present disclosure. To facilitate opening 231 and thusly access to the interior volume 234, fixture 202 has one or more hinges 236 that permit an arm 238 of fixture 202 to deflect and/or move about a pivot point, axis 240, 242, 244, and/or plane. Said differently, arm 238 is hingedly connected to fixture 202 about one or more hinges 236. Interior volume 234 is defined by interior surface 235.

The bore 208 has a size similar to that of a predetermined sample 204. For instance, known tampons have a diameter of between about 0.48 inches to about 0.63 inches (or about 12 mm to about 16 mm) and a length of about 1.25 to about 3 inches. Other known internally worn menstrual devices, such as cups have a diameter of about 1 inch while others have a diameter of up to 3 inches. As such, bore 208 is sized similarly to samples 204 of these devices. Alternatively, bore 208 is sized to emulate the in vivo environment. By way of example, the bore 208 is suitably configured to receive an internally worn hygiene device, such as a tampon, and as such, is sized and shaped similarly to any known vaginal cavity anatomy and/or mean, median, mode or otherwise representative dimensions.

FIGS. 1-4 exemplify a bore 208 generally disposed along the central vertical axis 240 of fixture 202, but can be in other locations depending on the configuration of the fixture 202. For instance, FIGS. 5-7 exemplify fixtures 202 having one or more contoured surfaces 281 and shapes more closely resembling at least one surface of the human body, more specifically, the pelvic region, and even more specifically, between the upper legs (or thighs), the vaginal, urethral, and/or buttocks regions.

The bore 208 may be configured to have a size that corresponds to a predetermined pressure that is applied to the sample 204 by the fixture 202. For example, bore 208 is configured to have a diameter 207 that is slightly smaller than the sample 204 of a device, such as a tampon, such that a predetermined bodily pressure is exerted along at least a portion of the sample 204 (and in some embodiments, along the entire axial length of the sample 204). For example, the fixture 202 applies at least one of a hydraulic pressure or a pneumatic pressure to the sample 204. To apply such pressure, a wrapper 212 is provided proximal, adjacent to and/or surrounding the sample 204. The wrapper 212 is made of a material having a low density that is sufficiently distinct from the fluid 246 density and/or sample 204 density, to avoid any imaging confusion with sample 204. The wrapper 212 is often positioned in close proximity to sample 204, so it is critical the wrapper 212 is radiographically discernable from the sample 204 and/or the fluid 246 contained within the wrapper 212. Such wrapper 212 materials include hydrophobic foams, closed cell foams, polyurethane, plastics, films and laminates, polyethylene, low density polyethylene, linear low density polyethylene, polyester, polypropylene, nylon and other long-chain carbon materials, etc. The system utilizes fluid of a predetermined viscosity. In some embodiments, the fluid has varying viscosity. In some embodiments, the fluid utilized to generate hydraulic or pneumatic pressure is non-Newtonian. The application of the pressure to the sample 204 may be done to simulate an application of bodily pressure to the sample 204 when the sample 204 (or an analogous sample) is inserted in a body cavity.

The pressure is preferably between about 0.1 psi to about 5 psi, and more preferably between about 0.25 psi and 1 psi. Such pressure can be exerted by the fixture 202 in its entirety to simulate an overall bodily pressure. Alternatively [or additively], such pressure can be exerted by a single aspect or member of the fixture 202 to simulate certain anatomical features that exude pressure against a sample 204. Further, other pressures exerted by, for instance, involuntary or voluntary bodily reactions, such as hiccups, sneezing, coughing, laughing, etc., can also create dynamic pressure (s). For example, the fixture 202 may provide a pressure of about 0.25 psi to simulate pressure of the body surrounding the vaginal canal, but may have an additional member 209 that adds an additional pressure simulating the pressure applied to the vaginal cavity by a full or partially full bladder. The additional member 209 in the fixture 202 can be located within and/or proximal the bore 208 such that it applies pressure directly to the sample 204 and/or indirectly to the sample 204. Additional member 209 can comprise a bladder and contain fluid, and can be dynamic (i.e. fluid volume in the bladder increases or decreases). The pressure exerted by the additional member 209 can be dynamic alone or in concert with the fixture 202 (i.e., where the fixture 202 applies dynamic pressure). Dynamic pressure can be described as pressure that changes over time. Dynamic pressure also includes, in certain embodiments, the force exerted outwardly by a consumer product as it absorbs and/or retains fluid (and thus expands or changes in size/shape).

Additional member 209 provides fixture 202 the opportunity to have a plurality of different pressures exerted by multiple different objects and/or fluids. For instance, a first pressure 209a is exerted on the sample 204 by fixture 202. A second pressure 209b is provided via fluid disposed or dispensed into a wrapper 212 surrounding and/or proximal to the sample 204 situated in or adjacent to the fixture 202 (i.e., in the bore 208 as shown in FIG. 3). A third pressure is provided via additional member 209 situated proximal the fixture 202 such that it exerts an additional force or pressure onto the fixture 202, causing the simulation of another environmental variable. In this embodiment, the fixture 202 simulates general bodily pressure. The additional member 209 simulates the environment of the vaginal canal. The additional member 209 simulates the pressure exerted within the body against the vaginal canal by the bladder.

In one embodiment, the fixture 202 permits expansion to accommodate studies of dynamic systems. The fixture 202 permits expansion to, for instance, permit a significant amount of pressure to be exerted (via the accumulation of fluid 246 in the bladder of additional member 209) while keeping the bladder within the fixture 202 and proximal the sample 204. The fixture 202 can comprise a material that is expandable or extensible or compressible such that it changes shape in response to the, for instance, bladder's shape. In embodiments where the fixture 202 material is compressible, it must remain radiotransparent upon compression. Advantageously, compressible structures can be structured to maintain the general shape and size of the footprint to ensure the system 200 isn't altered.

In embodiments where the fixture 202 is expandable or extensible, it can be due to the material properties of the fixture 202 itself, and/or the physical structure. For instance, and as exemplified in FIGS. 1 and 2, the fixture 202 can have arms 238 that deviate in position upon expansion of the sample 204 and/or due to the expansion of additional member(s) 209.

In further embodiments, the fixture 202 has one or more retaining straps 214. In a first embodiment, the one or more retaining straps 214 are extensible thereby permitting expansion/deflection after a certain level of force is reached (i.e., a force exceeding the force exerted by the retaining strap(s) 214). This can be advantageous in set-ups where deflection is useful for inserting samples 204 into (or adjacent to, or onto the fixture 202) and/or modifying the fixture 202 to perform in a certain manner, while ensuring the fixture 202 remains substantially static with respect to the platform 216 during the test.

In some embodiments, the one or more retaining straps 214 can be positioned to provide pressure to the fixture 202 to simulate bodily pressures in addition to, in lieu of, or to support pressures exerted by other portions or structures of the fixture 202. The one or more retaining straps 214 can be placed around a portion of the fixture 202 to exert a specific pressure around a portion of the length, width and/or height of the sample 204. The one more retaining strap 214 can be placed around a portion of the fixture 202 to exert a specific pressure adjacent a sample 204, such as proximal to the inferior sample end and/or the superior sample end, the sample forward end, the sample rearward end, etc. In these embodiments, a pressure adjacent the sample 204 can simulate the sample's 204 performance in vivo, modeling the pressure applied by external anatomy, such as limbs (i.e. arms or legs), by internal anatomy, such as the cervical os, the bladder, the vaginal wall, the introitus, and/or by garments, such as underwear, pants, etc.

In a second embodiment, the one or more retaining straps 214 are substantially rigid. In this embodiment, the fixture 202 remains substantially static during the test, but permits access or modification to the fixture 202 before and after the test.

The one or more retaining straps 214 can be a unitary structure, such as an elastomeric band or tape. The one or more retaining straps 214 can also have a clasp 213 permitting adjustment of the one or more retaining straps 214 to modify pressure around at least a portion of fixture 204. The one or more retaining straps 214 can be attached and/or positioned on or surrounding a portion of fixture 202, or can be attached to platform 216, or combinations thereof.

Figure 7:
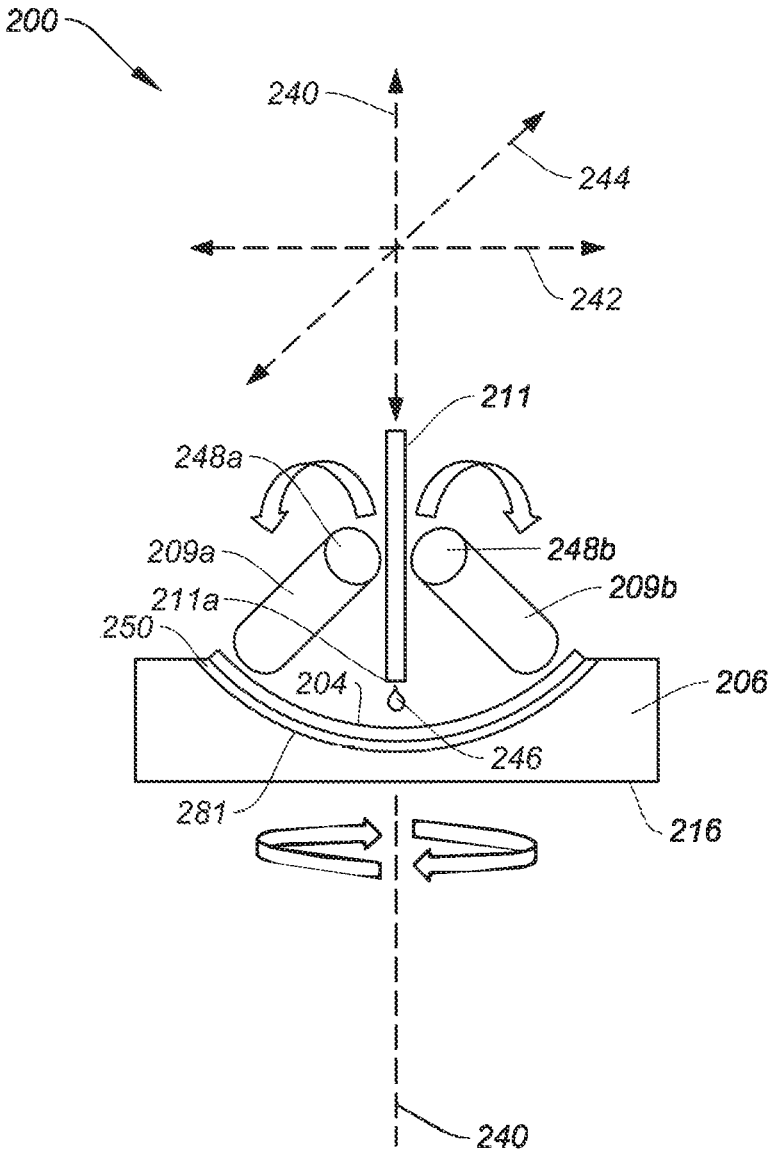
FIG. 7 illustrates a diagrammatic representation of one embodiment of the present disclosure's test fixture apparatus.

The fixture 202 may include a fluid source 210 that is configured to introduce/apply a fluid 246 to the sample 204 by a line 211 coupling the fluid source 210 and the sample 204 in FIG. 7. Fluid source 210 is attachable to system 200, to fixture 202, and/or to platform 216. The fluid 246 provided by the fluid source 210 may be of any type or composition, such as water, menses, blood, synthetic menses, glycerin, etc., or a mixture of one or more of the aforementioned fluids. In some embodiments, a dye may be used in the fluid 246. The fluid 246 may be selected to have a density that is sufficiently distinct from the density of the fixture 202 (in an amount greater than a threshold), such that the fluid 246 and the fixture 202 can be distinguished from one another via imaging technology. In some embodiments, the fluid 246 density is significantly distinct from a density of the fixture 202. In some embodiments, the fixture 202 may be clear/see-through/translucent to a user's naked eye (to facilitate a visual inspection of the sample 204 when the sample is retained in the fixture 202), such that the fixture 202 may be optically transparent. However, in some embodiments the fixture 202 might only be radiographically transparent/translucent.

Starting with a dry sample 204, the fixture 202 may cause the fluid source 210 to apply fluid 246 to the sample 204 until the sample 204 is saturated.

The fixture 202 may include a wrapper 212. The wrapper 212 may retain the sample 204 in the bore 208 of the retaining mechanism 206. The wrapper 212 encompasses at least a majority of an outer periphery of said fixture 202. To the extent fluid 246 escapes the sample 204 and/or is meant to surround sample 204, the wrapper 212 may prevent fluid 246 from the fluid source 210 leaking onto/into the retaining mechanism 206/bore 208 by creating a barrier between the bore 208, the opening 231 and/or the fixture 202 in general that substantially keeps fluid inside the wrapper 212.

Figure 5:
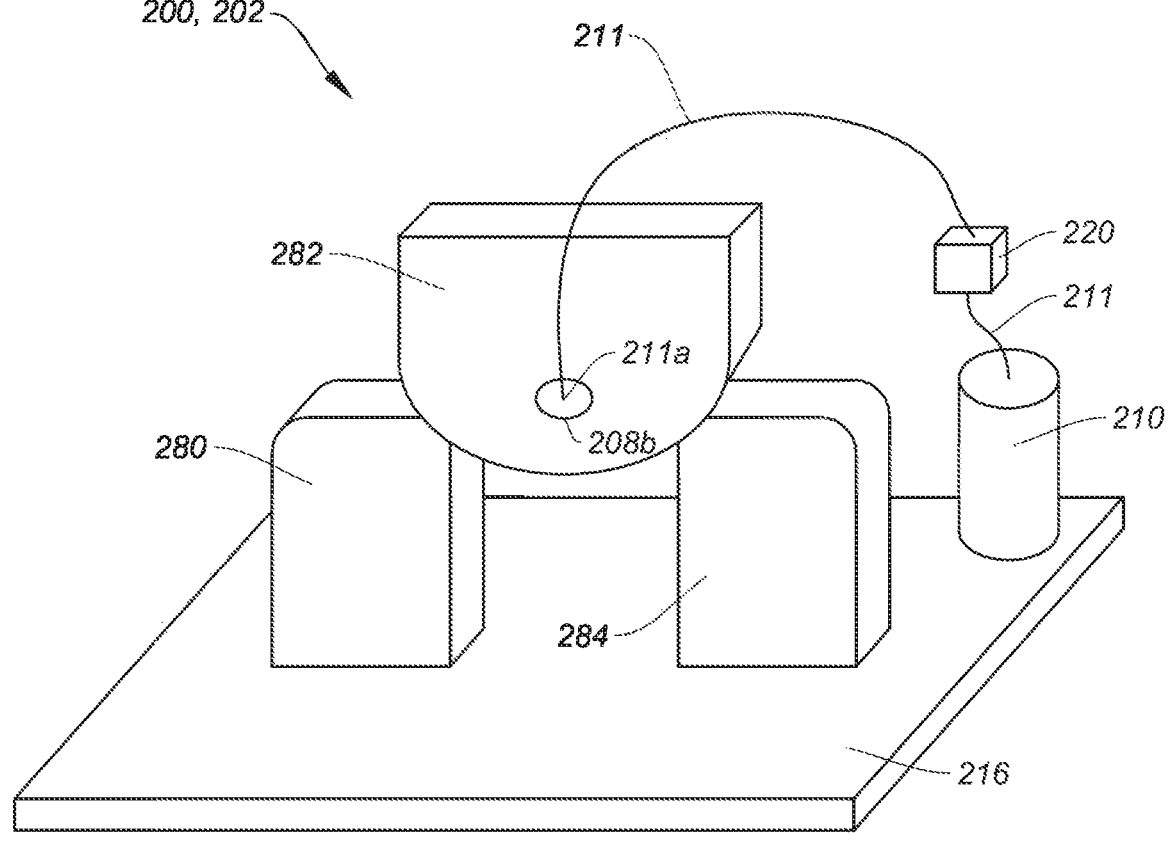
FIG. 5 illustrates a diagrammatic representation of one embodiment of the present disclosure's test fixture apparatus.
Figure 6:
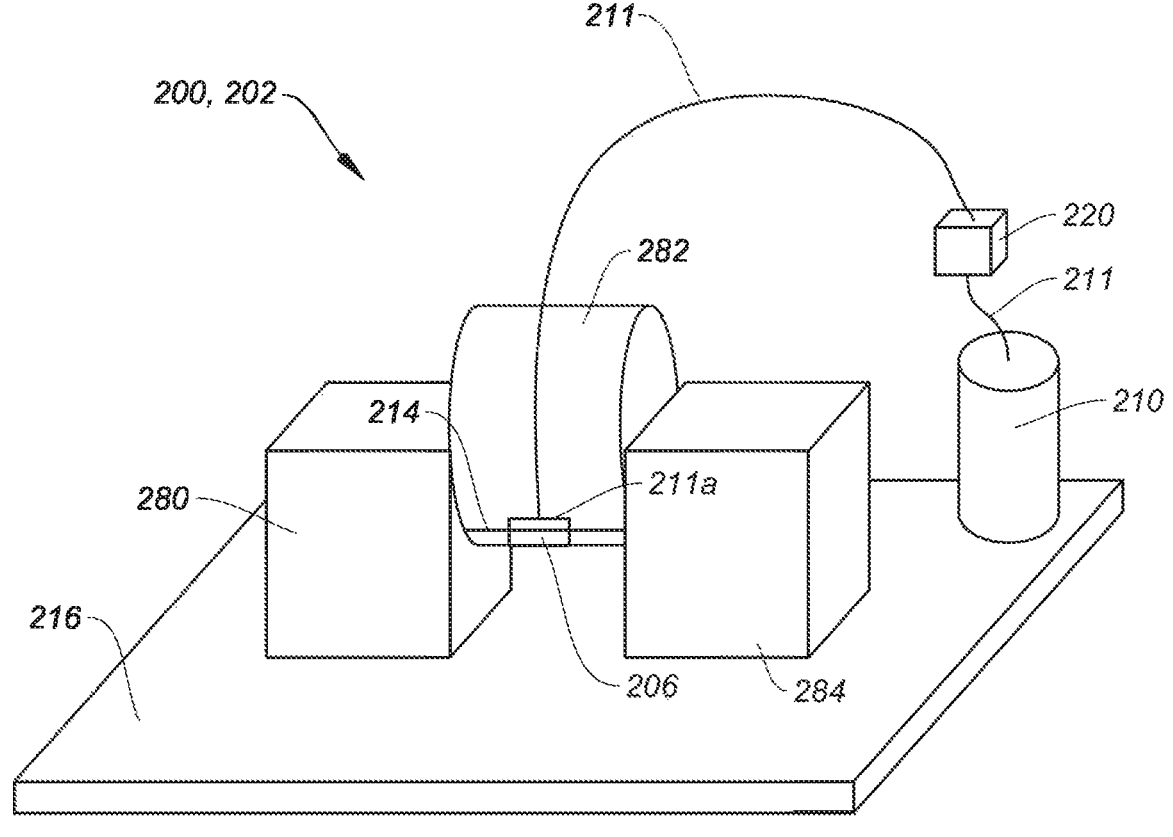
FIG. 6 illustrates a diagrammatic representation of one embodiment of the present disclosure's test fixture apparatus.

FIGS. 5-7 provide an additional aspect of the present disclosure, where the fixture 202 and/or retaining mechanism 206 are configured to more specifically replicate an in vivo set-up. As shown in FIGS. 5-6, fixture 202 includes a first region 280, a second region 282, and a third region 284. The first region 280, second region 282 and third region 284 can be fixed and stationary (with respect to each other) or movable and dynamic (with respect to each other) The first region 280 and the third region 284 support second region 282, and/or simulate a portion of the human body. First region 280 and third region 284 provide support for second region 282, and as such, resemble limbs such as legs in an in vivo setup. Second region 282 provides a contoured surface 281. Second region 282 has a contoured surface 281 emulating at least one surface of an in vivo setup. First region 280 and/or third region 284 may also have contoured surfaces to further simulate an in vivo setup.

FIG. 7 provides a retaining mechanism 206 holding sample 204 adjacent the body. Retaining mechanism 206 optionally includes one or more retaining straps 214 (and optionally one or more clasps 213). Barrier 250 is adjacent retaining mechanism 206 on a surface facing fixture 202 which is adjacent sample 204. Barrier 250 is integral with retaining mechanism 206 and/or attachable to retaining mechanism 206. Barrier 250 optionally has varying surface topography to simulate vaginal rugae and/or other anatomical features of the body.

FIG. 5 provides a bore 208 that is internal to fixture 202. In this embodiment, bore 208 provides a means for retaining and/or directing line 211 (and line end 211a) into a location that simulates the urethra or vaginal cavity. In such embodiments, line 211 and line end 211a is positioned with respect to sample 204 to simulate fluid flow in an in vivo setup. In further embodiments, bore 208 extends through fixture 208 such that line 211 runs internally through fixture 202: bore 208 has a first opening (not shown) where line 211 enters and a second opening 208b where line end 211a deposits fluid 246 onto or proximal to sample 204. In further embodiments, bore 208 simulates an internal body cavity, such as the vaginal cavity. In other embodiments, line 211 is positioned external to fixture 202 and attachable at least at a position similar to where the urethra or vaginal opening would be in an in vivo setup such that fluid 246 exits line end 211a at an appropriate location proximal to or on sample 204.

Figure 8A:
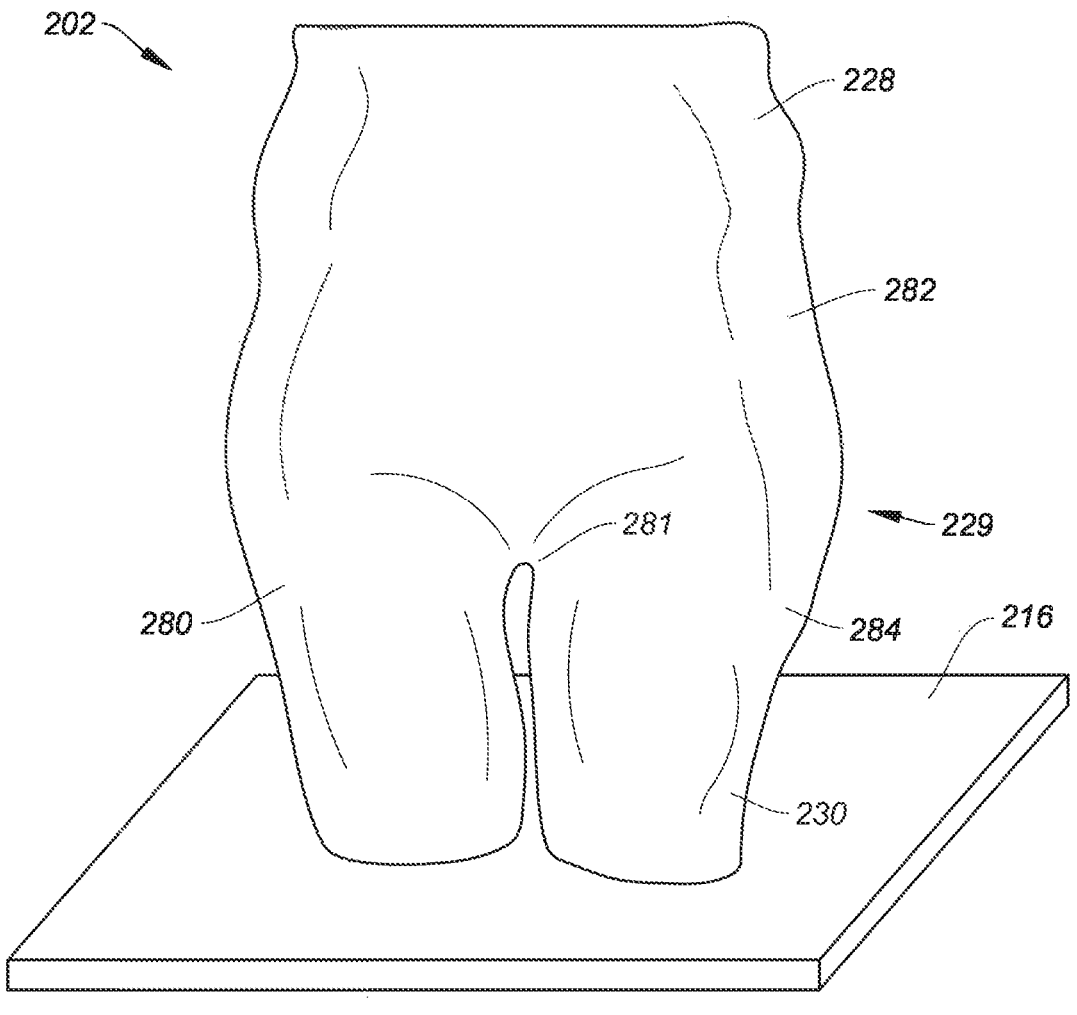
FIG. 8A illustrates a diagrammatic representation of one embodiment of the present disclosure's test fixture apparatus.
Figure 8B:
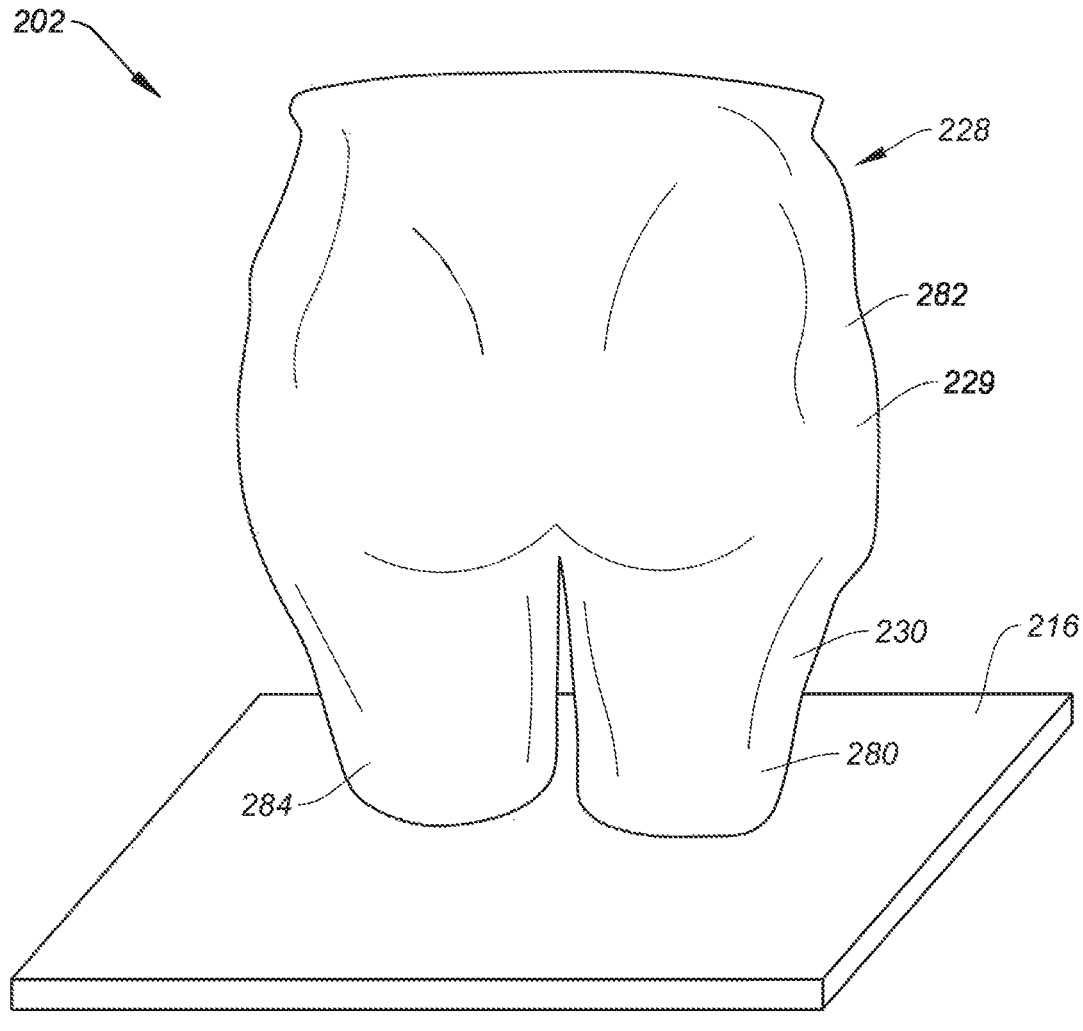
FIG. 8B illustrates a diagrammatic representation of a back view of one embodiment of the present disclosure's test fixture apparatus.
Figure 8C:
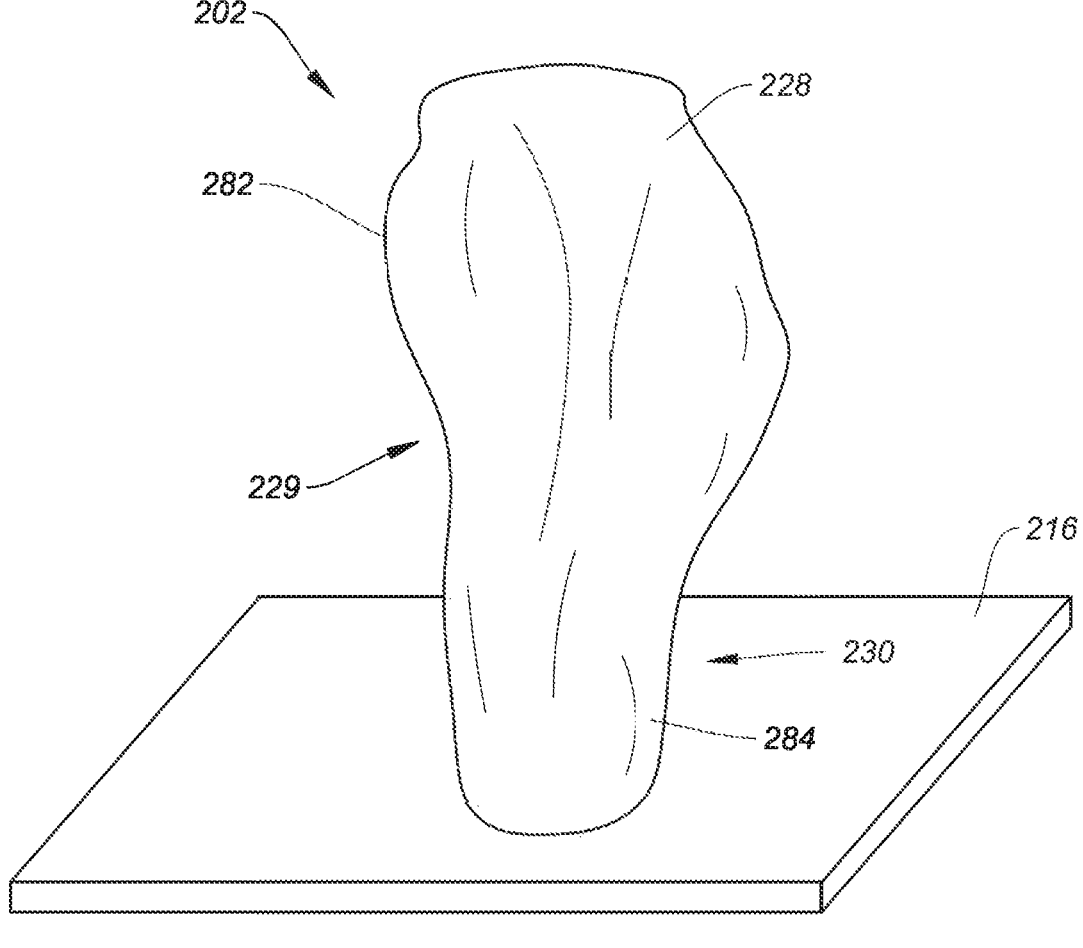
FIG. 8C illustrates a diagrammatic representation of a side view one embodiment of the present disclosure's test fixture apparatus.

FIGS. 8A-8C provide various views of a fixture 202 emulating the midsection of a person. The description provided for FIGS. 5-7 also holds true with these embodiments exemplified by FIGS. 8A-8C. Fixture 202 has a first region 280, second region 282, and a third region 284. Fixture 202 replicates a human body. Fixture 202 is, for example cut from a radiotransparent material, such as foam by a CNC machine that has inputted data from a human body scan. The CNC machine cuts individual slices of the radiotransparent material which are thereafter connected by adhesive, one or more retaining straps, etc. The CNC machine can optionally create bore 208 such that it also resembles the human body (i.e., the vaginal cavity). In this manner, fixture 202 can simulate both internal and external human anatomy and thus fixture 202 provides the opportunity to have an in vitro setup that even more closely resembles an in vivo one.

Figures 10, 11:
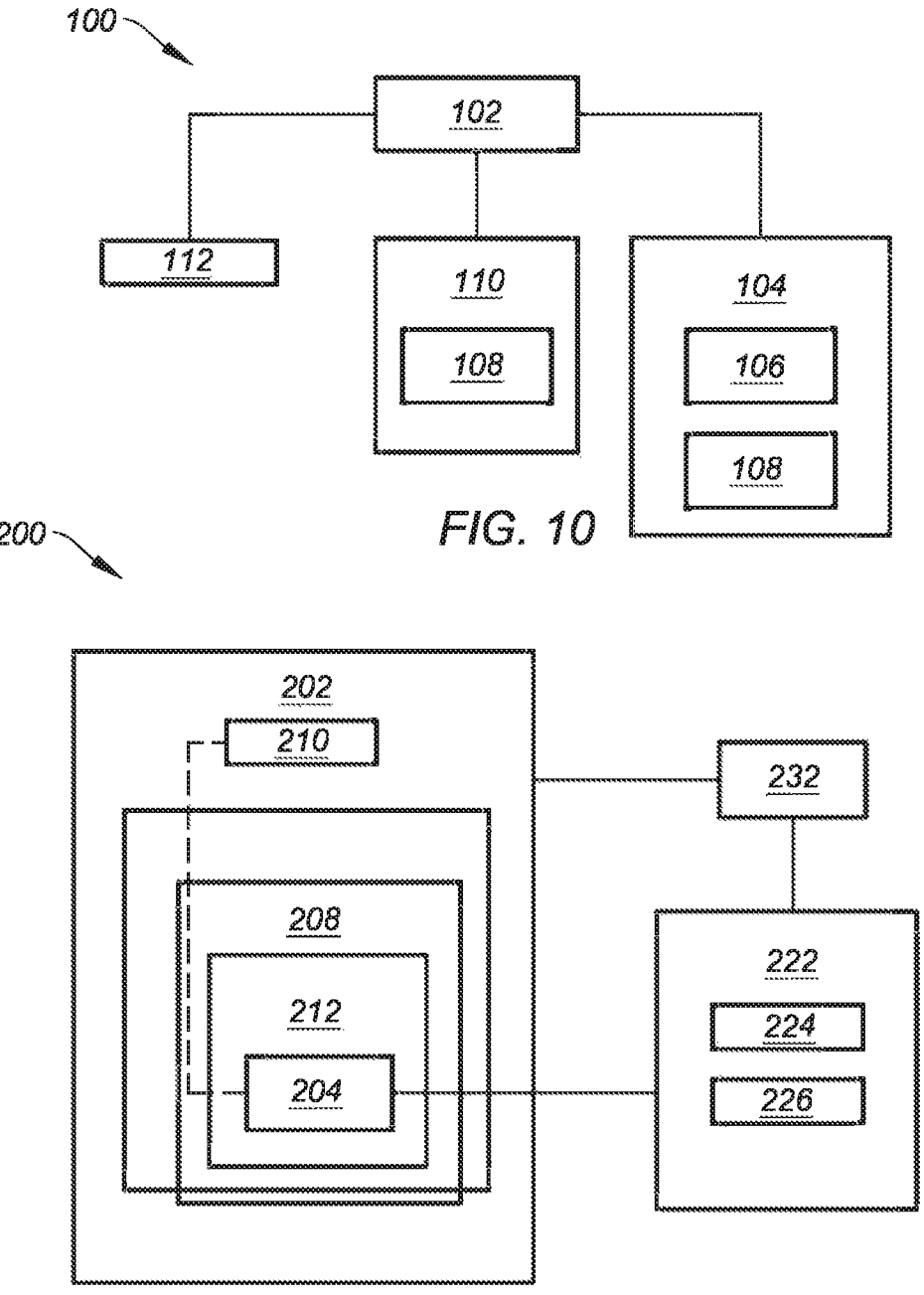
FIG. 10 illustrates a computing system architecture.
FIG. 11 illustrates a system that is configured to represent a fluid or fluid flow associated with a sample.
Figure 12A:
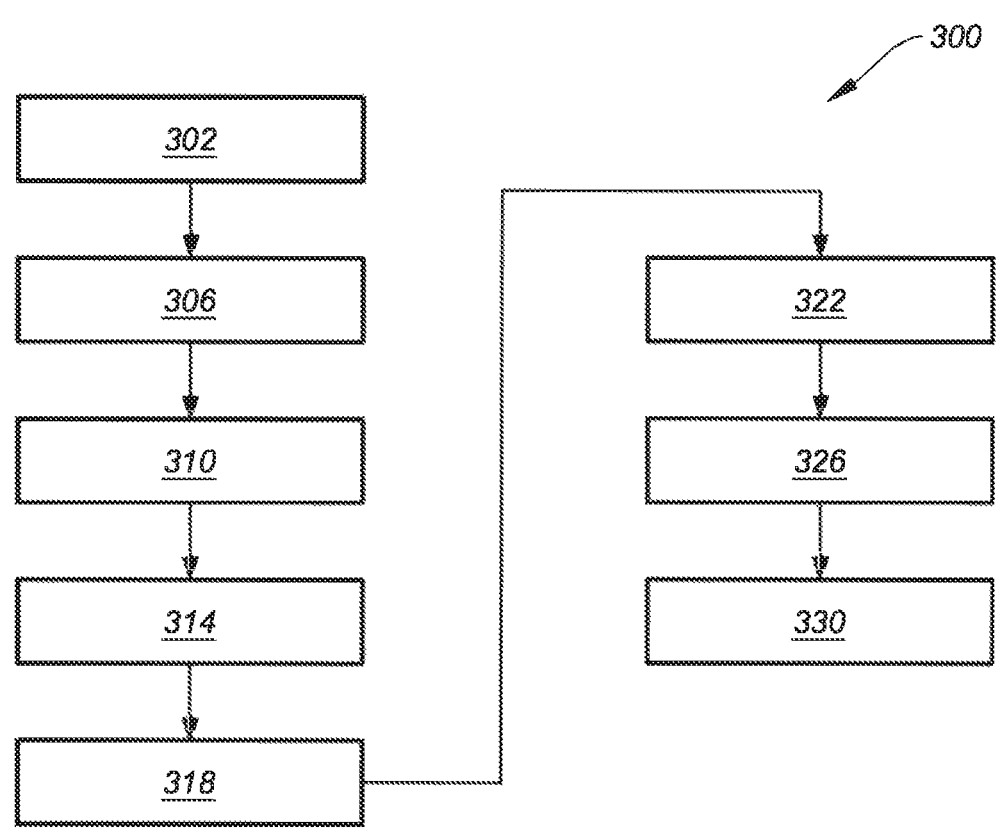
FIGS. 12A-12E illustrate a flow chart of an exemplary method for representing a fluid or fluid flow associated with a sample.
Figure 12B:
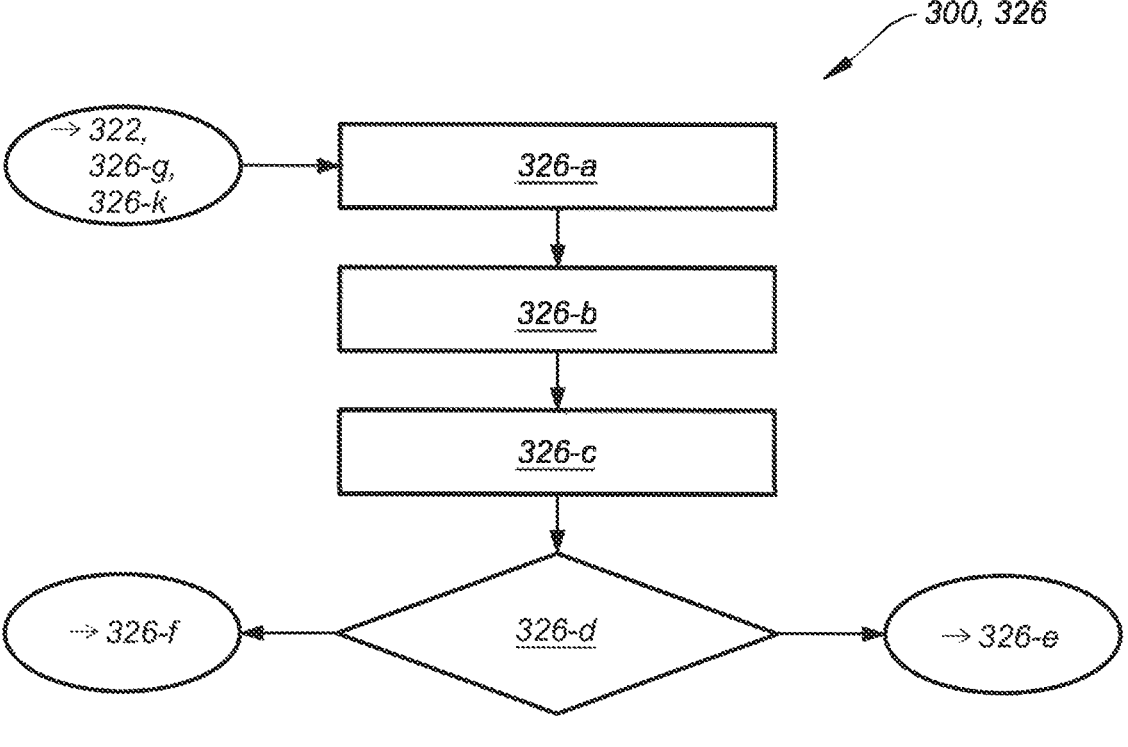
Figure 12C:
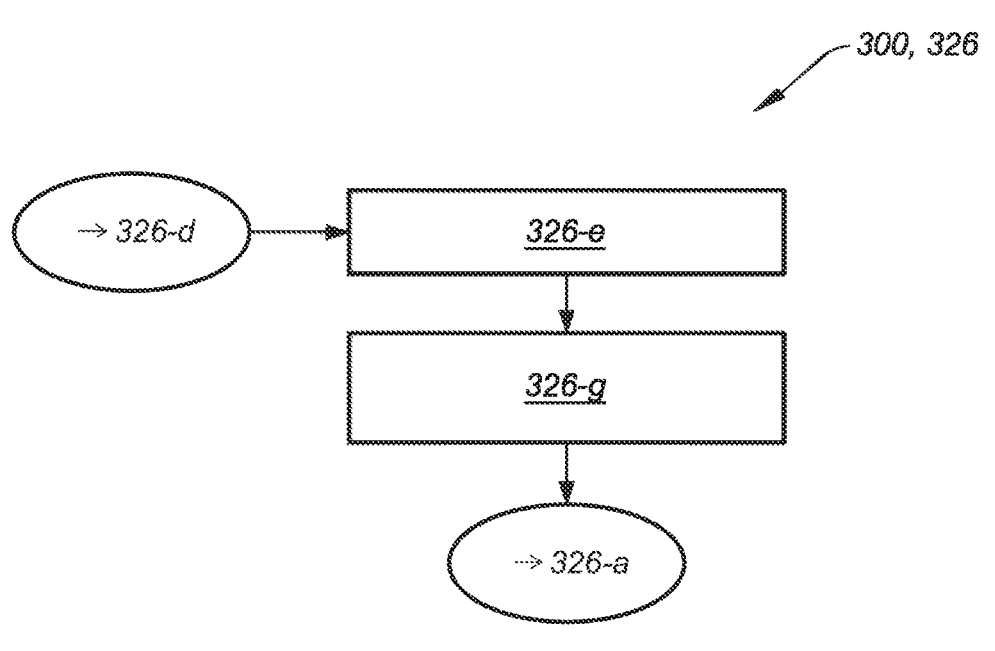
Figure 12D:
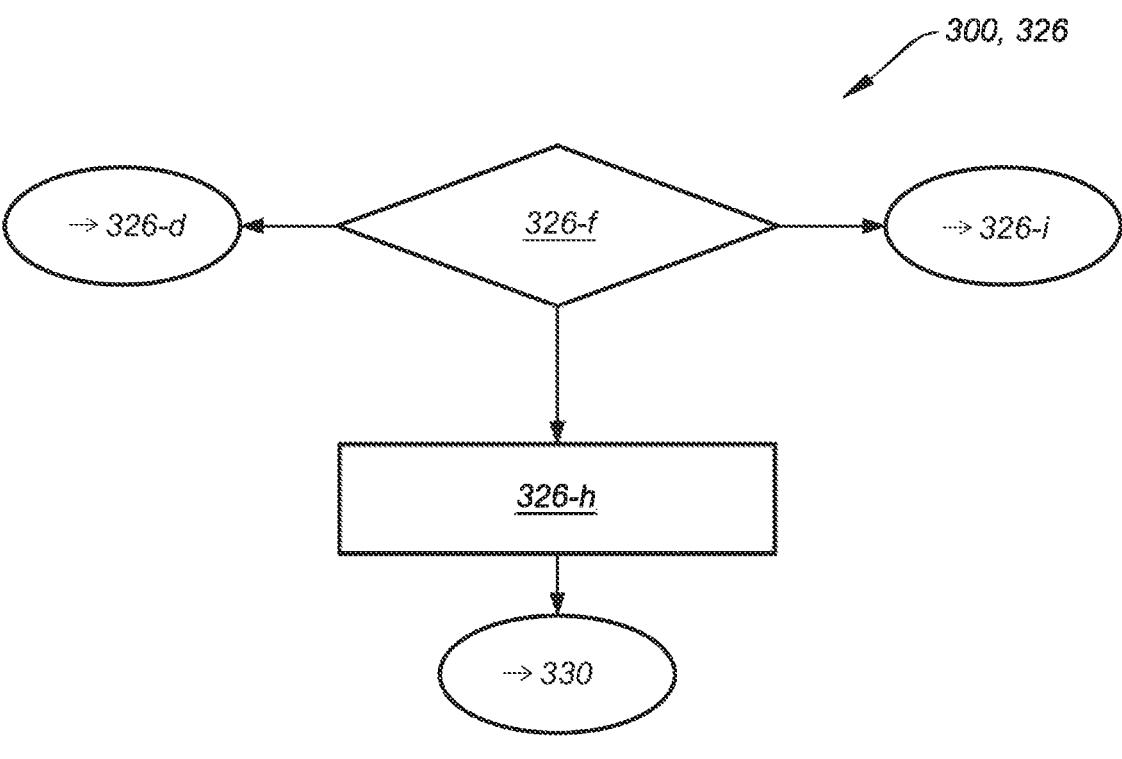
Figure 12E:
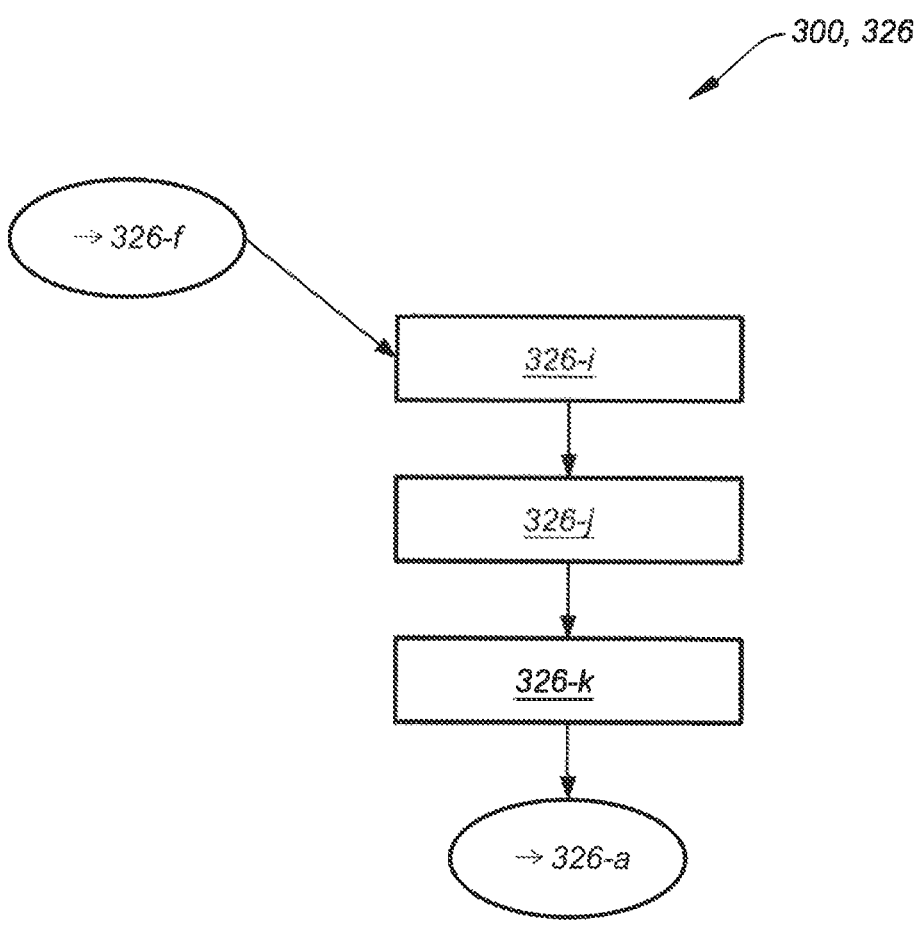

Referring now to FIG. 10, an illustrative system 100 is shown. The system 100 may be associated with one or more computers. The system 100 includes one or more processors (generally shown by a processor 102) and a memory 104. The memory 104 may store data 106 and/or instructions 108. The system 100 may include a computer-readable medium (CRM) 110 that may store some or all of the instructions 108. The CRM 110 may include a transitory and/or non-transitory computer-readable medium.

The instructions 108, when executed by the processor 102, may cause the system 100 (or one or more portions thereof) to perform one or more methodological acts or processes, such as those described herein. As an example, execution of the instructions 108 may cause: one or more images of a sample to be captured based on an introduction/application of a fluid 246 to the sample 204, a data set to be obtained/generated based on the one or more images, and an analysis to be performed based on the data set to determine a grayscale value that represents a fluid 246 flow.

The data 106 may include the images, the data set or additional data based on an analysis of the data. In some embodiments, the data 106 may be associated with one or more programs, such as a modeling or simulation program. For example, the data may be native to or supported by one or more computed aided design or computer aided drawing programs, either one or both of which may be referred to as CAD programs.

The system 100 may include one or more input/output (I/O) devices 112 that may be used to provide an interface between the system 100 and one or more additional systems or components. The I/O devices 112 may include one or more of a graphical user interface (GUI), a display screen, a touchscreen, a keyboard, a mouse, a joystick, a pushbutton, a microphone, a speaker, a microphone, a transceiver, a sensor, etc.

Referring now to FIG. 11, the system 200 includes an imaging device 222. The imaging device 222 may take/ acquire one or more images of the sample 204, such as when fluid 246 from the fluid source 210 is applied to the sample 204. The frequency with which the one or more images are taken can be dependent on the viscosity of the fluid 246 and/or the properties of the sample 204. In other words, a fluid 246 having a higher viscosity may travel more slowly through the sample 204, and as such, time between images may be longer without missing meaningful data sets. Alternatively, a sample 204 having greater porosity, permeability, wicking rates, etc. may require more frequent imaging to fully capture data sets that will demonstrate fluid 246 movement within sample 204. In some embodiments, sample 204 has multiple different materials and/or rates and the configuration of such materials in sample 204 require varying rates with which images are taken. For instance, images may need to be taken more quickly as fluid 246 is introduced into a wicking layer or highly permeable area of the sample 204, and thereafter, slower time intervals for taking images may be sufficient as the fluid 246 travels more slowly through less permeable absorbent areas of the sample 204. The skilled artisan understands that time intervals may vary more complexly than described herein. In some embodiments, images are taken less than one minute apart. In further embodiments, images are taken about ten to fifteen seconds apart. In further embodiments, images are taken less than ten seconds apart.

In some embodiments, the fixture 202 or a portion thereof (e.g., the retaining mechanism 206) may rotate in order to cause the sample 204 to rotate. The rotation may occur at a predetermined rate. The rotation may occur when the images are acquired by the imaging device 222. Alternatively, or additionally, the imaging device 222 may rotate relative to the fixture 202/sample 204. Relative rotation enables capturing multiple views of the sample 204 during the test. In some embodiments, the fixture 202 is placed upon and/or attached to the platform 216. The platform 216 is a rotatable surface 216a (i.e., a turntable) in at least one plane (i.e., the x-y plane, the y-z plane, and/or the x-z plane) and/or optionally in at least two planes (i.e., a shaker table). In other embodiments, the fixture 202 is attached to a gimbal 216b, 216c (as represented by both solid and dashed lines in FIG. 9) permitting dynamic movement in multiple planes or about multiple axes. The platform 216 (i.e., rotatable surface 216a or gimbal 216b, 216c) assists the imaging device 222 in visually capturing the sample's 204 performance during the test.

Figure 9:
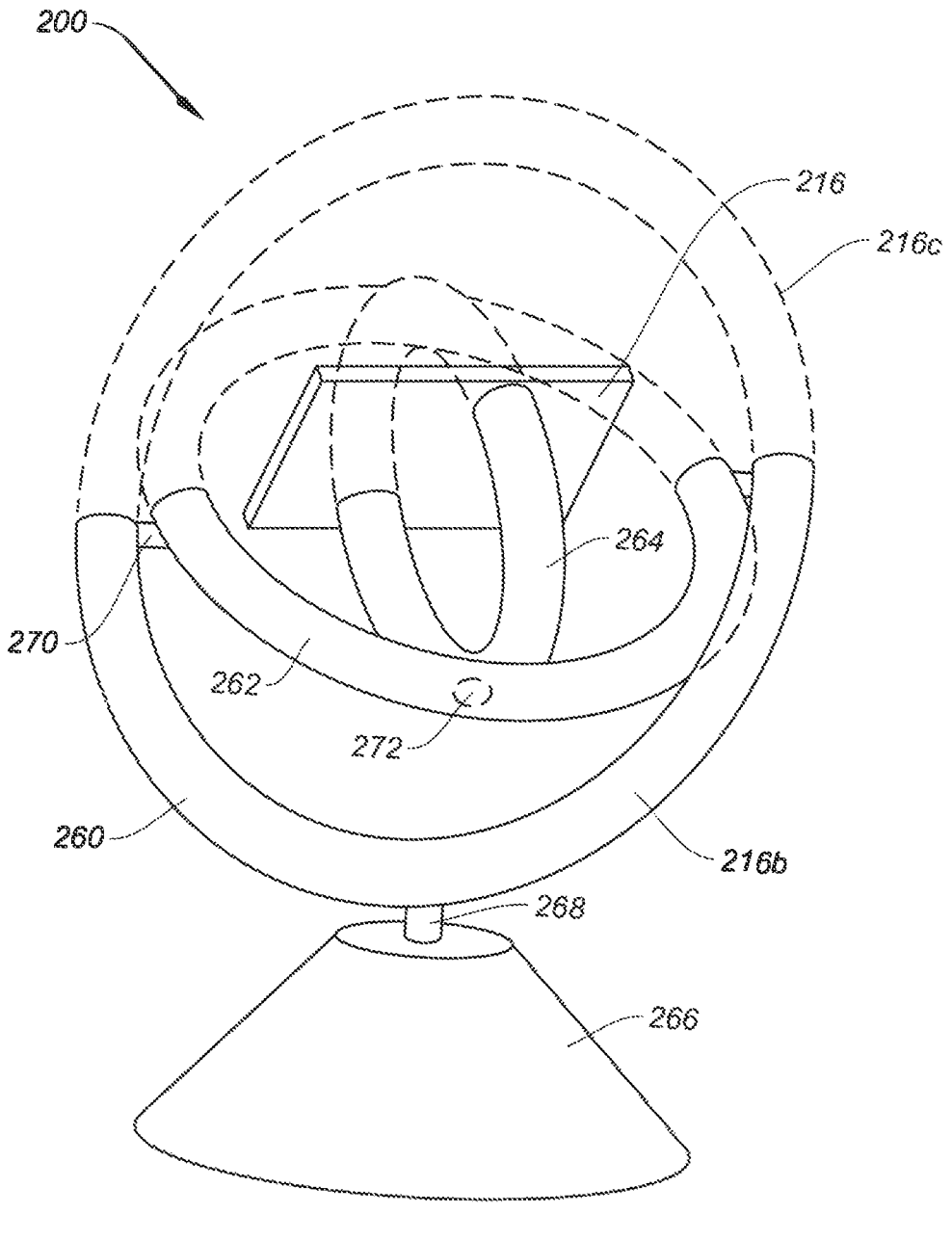
FIG. 9 illustrates a diagrammatic representation of a side view one embodiment of the present disclosure's test fixture apparatus.

As shown in FIG. 9, gimbal 216b, 216c has a first linkage 260, a second linkage 262 and a third linkage 264, where the first linkage 260 and second linkage 262 are connected and/or movable about each other at joint 270. Second linkage 262 and third linkage 264 are connected and/or movable about joint 272. Gimbal 216b, 216c is stabilized by base 266. Gimbal 216b, 216c is connected directly to base 266 or by shaft 268. The aforementioned configuration permits rotation amongst first linkage 260 and second linkage 262, and second linkage 262 and third linkage 264. In total, it permits angular rotation of platform 216 and thusly fixture 202 and sample 204.

In some embodiments, a partial gimbal 216b is provided to permit relative rotation between the sample 204 that is proximal to the fixture 202 (i.e., within or adjacent the fixture 202) and the imaging while not obstructing the imaging device 222 or any other features connected to the fixture 202. A partial gimbal 216b is exemplified by the solid lines in FIG. 9. For instance, the partial gimbal provides three dimensional rotation in a partial sphere such that other features can be positioned or connected to the test fixture 202 in areas where there is no movement. Although rotation is restricted with a partial gimbal, it still provides the ability to study the sample 204 in simulated conditions (i.e., shifting of a sample 204 during a person's gait, the sample's 204 response to one or more dynamic bodily pressures, etc.). In some embodiments, the partial gimbal is a half gimbal. In other embodiments, a full gimbal is provided (as indicated by the solid and dashed lines in FIG. 9).

In some embodiments, rotation about at least one axis 240, 242, 244 simulates relative in vivo movement of a person and the device. For instance, and with respect to products worn on or internally to the body during physical motion, a typical gait for a person is about three miles per hour. As such, depending on the size of the fixture 202, the fixture 202 rotates about at least one axis 240, 242, 244 at rate of about 52 in/second. As people typically move at speeds between 0.1 mph and about 25 mph, the fixture 202 is capable of rotating at speeds between about 1.7 in/second to about 806 in/second, or perhaps more typical for most people partaking in exercise, speeds between about 52 in/second to about 176 in/second.

As shown in FIG. 7, dynamic pressure can be applied via additional members 209a and 209b. Additional members 209a, 209b articulate about joint 248a, 248b, respectively. Additional members are capable of applying a static pressure as well. Additional members 209a, 209b apply pressure in at least one plane, or by articulating about at least one axis 240, 242, 244. Such articulation can work in concert with the movement of fixture 202 or retaining mechanism 206 on platform 216. For instance, additional members 209a and 209b can simulate rubbing amongst body parts, such as limbs and the torso, or more specifically, the legs and the pelvic region, while a sample is being worn externally as shown in FIG. 7 (or internally as demonstrated throughout the specification). Movement of additional members 209a, 209b can be done to simulate bodily pressures exerted amongst body parts at a rate similar to that of a person walking, running, or participating in athletics, as described in the present disclosure. In certain embodiments, barrier 250 separates the retaining mechanism 206 (or fixture 202, in other embodiments) and sample 204 such that any fluid 246 escaping the sample 204 does not saturate and/or soil retaining mechanism 206 (or fixture 202). This simplifies cleaning and As such, barrier 250 is an impermeable material that is preferably maintenance, radiotransparent, or at the very least, has a density sufficiently distinct from the sample 204 and/or fluid 246. Some examples of materials include silicon and other plastics and foams mentioned throughout the present disclosure. Such a barrier 250 can be applied to any of the exemplary fixtures of the present disclosure.

A modified syngyna test methodology can be used in ascertaining fluid handling performance and absorbent characteristics of the sample 204. Such a set-up includes a syringe pump 220 moving fluid 246 from a fluid source 210, such as a beaker, bag and/or graduated cylinder, to a line 211 located proximal to the sample. The line 211 has a line end portion 211a that dispenses (i.e., drips) fluid 246 at a predetermined rate controlled by the syringe pump 220. The components of the line 211 and line end portion 211a must be material that will not disrupt the imaging and as such, should be made from a material that is sufficiently distinct from sample 204 and/or fluid 246. Preferably, the line and end portion are radio transparent. For instance, the rate is between about 10 ml/hr to about 70 ml/hr, or more preferably, between about 20 ml/hr to about 50 ml/hr, or even more preferably, about 25 ml/hr for internally worn menstrual products and about 50 ml/hr for externally worn hygiene products, such as menstrual or incontinence underwear, diapers, napkins, pads, and/or liners.

The imaging device 222 may be operative in accordance with one or more imaging technologies. For example, the imaging device 222 may be operative in accordance with at least one of computed tomography, magnetic resonance imaging, nuclear magnetic resonance imaging, or magnetic resonance tomography. In some embodiments, the imaging device 222 may include an imaging source 224 and an imaging detector 226. The imaging source 224 and the imaging detector 226 may be operative in accordance with x-ray technology.

The system 200 includes a computer 232. The computer 232, which may include one or more of the components/ devices described above in connection with the system 100 of FIG. 10, may be configured to coordinate or synchronize the activities of the fixture 202 and the imaging device 222. The computer 232 may also perform one or more of the methodological acts described herein. For example, the computer 232 may obtain one or more images from the imaging device 222, obtain one or more data sets based on the images, and perform an analysis in connection with data set(s) to determine a grayscale value that represents a fluid flow through the sample 204.

In some embodiments, one or more time stamps (e.g., a scanning time) may be associated with the images acquired by the imaging device 222. The time stamps may be used to generate a four-dimensional data set associated with a fluid flow in the sample 204. The four-dimensional data set may be obtained by generating a three-dimensional data set based on the images acquired by the imaging device 222 and applying the time stamps to the three-dimensional data set.

In some embodiments, one or more radiographs may be acquired by the imaging device 222. A radiograph may represent a two-dimensional projection as interpreted by a detector of the imaging device 222. A three-dimensional reconstruction may be generated based on a synthesis of a plurality of radiographs. A four-dimensional reconstruction may be generated based on an application of the time stamps to the three-dimensional reconstruction.

The systems 100 and 200 are illustrative. In some embodiments, one or more of the components or devices may be optional. In some embodiments, the components/devices may be arranged in a manner that is different from what is shown in FIGS. 10 and 11. In some embodiments, additional components or devices not shown may be included. For example, in embodiments where the system 100 or the system 200 is included as part of one or more networks, one or more switches, routers, and the like may be included. One or more portions of the system 100 or the system 200 may be included in a particular computing device, such as a server, a personal computer, a laptop, a mobile device (e.g., a smartphone), etc.

As described above, the systems 100 and 200 may be used to obtain a grayscale value representative of a fluid flow in the sample 204. Referring to FIGS. 12A-12E (collectively referred to as FIG. 12) a flow chart of a method 300 is illustrated for obtaining such a grayscale value. The method 300 may be executed in conjunction with the system 200, or a portion thereof.

In block 302, a data set may be obtained based on a plurality of images acquired by, e.g., the imaging device 222 of FIG. 11. The data set obtained in block 302 may by a four-dimensional data set/reconstruction.

In block 306, an estimate is obtained regarding a grayscale value that is representative of the fluid flow. The estimate may be based on a user input to the system 200 of FIG. 11.

In block 310, a theoretical (volumetric) flow rate of the fluid is obtained. The theoretical flow rate may be based on a user input to the system 200 of FIG. 11.

In block 314, a "previous grayscale variable" may be defined. As part of block 314, the previous grayscale variable may be initialized/set to the estimate of the grayscale value obtained in block 306.

In block 318, a "current grayscale variable" may be defined. As part of block 318, the current grayscale variable may be initialized/set to the estimate of the grayscale value obtained in block 306.

In block 322, an "adjustment variable" may be defined. As part of block 322, the adjustment variable may be initialized/ set equal to an "adjustment value". For reasons that will become more apparent to a skilled artisan in view of the disclosure provided below, the adjustment value may be selected based on a degree of accuracy that is required and may be representative of a time it takes for the method 300 to converge to a final grayscale value representative of the fluid flow.

One skilled in the art will appreciate that the labels applied to the variables in connection with the blocks 314-322 are merely illustrative and the naming convention used is merely intended to signify the nature or use of the variables. One skilled in the art would appreciate that a more generic naming convention could be used (e.g., first variable, second variable, etc.) without departing from this disclosure.

In connection with block 326, a number of sub-blocks/ operations may be iteratively performed to arrive at, or converge to, a final grayscale value representative of the fluid or fluid flow: Block 326 is described in further detail below in connection with FIGS. 12B-12E.

In block 326-a (see FIG. 12B), a volume may be calculated for the data set of block 302 based on the current grayscale variable. As part of block 326-a, a determination may be made regarding a volume of what is intended to be the fluid as a function of length (e.g., radial axis 242, 244) for every data set/reconstruction of block 302. This may be done by adding up the volume of each voxel in each layer of the reconstruction whose grayscale value is between the current grayscale variable and an upper bound whose value is fixed relative to the current grayscale variable. As an illustrative example, if the current grayscale variable has a value of 1.34, and an upper bound offset is equal to 2.20, the upper bound may be equal to 1.34+2.20=3.54.

In block 326-b, a flow rate may be calculated based on the volume calculated in block 326-a. As part of block 326-b, a linear regression may be used to calculate the flow rate. The flow rate may be based on a derivative of a curve formed with: (A) volume as a dependent variable, and (B) imaging (e.g., scanning) time as an independent variable.

In block 326-c, an error may be calculated as a difference between the calculated flow rate of block 326-b and the theoretical flow rate of block 310. The error calculation of block 326-c may be conducted on an absolute value basis, such that the sign/polarity in the error may be disregarded.

In block 326-d, a comparison may be made to determine whether the error calculated in block 326-c is less than a threshold. The threshold may be based on, or correspond to, the error calculated in block 326-c during a previous iteration associated with block 326. If the error is less than the threshold, flow may proceed from block 326-d to block 326-e (see FIG. 12C). Otherwise (e.g., the error is greater than or equal to the threshold), flow may proceed from block 326-d to block 326-f (see FIG. 12D).

In block 326-e (see FIG. 12C), the previous grayscale variable may be set equal to the current grayscale variable.

In block 326-g, the current grayscale variable may be modified based on the adjustment variable. For example, as part of block 326-*g* the adjustment variable may be subtracted from the current grayscale variable to generate an updated current grayscale variable. Flow may proceed from block 326-*g* to block 326-*a*.

In block 326-*f* (see FIG. 12D), a comparison may be made to determine whether the adjustment variable is less than a (second) threshold. This threshold may be based on a resolution associated with the system (e.g., system 200) that is used. The threshold may be based on a user input. The threshold may serve as a factor in the time it takes for the method 300 to converge to a final grayscale value representative of the fluid flow: a smaller value of the threshold (representative of a fine resolution) may result in a longer convergence time relative to a larger value (representative of a coarse resolution), all other things being equal. The threshold may correspond to a predetermined value associated with an accuracy resolution. If it is determined in block 326-*f* that the adjustment variable is less than the threshold, flow may proceed from block 326-*f* to block 326-*h*. Otherwise (e.g., the adjustment variable is greater than or equal to the threshold), flow may proceed from block 326-*f* to block 326-*i* (see FIG. 12E).

In block 326-*h*, the iteration associated with block 326 may end. Flow may proceed from block 326-*h* to block 330 (see FIG. 12A).

In block 326-*i* (see FIG. 12E), the previous grayscale variable may be set equal to the current grayscale variable.

In block 326-*j*, the adjustment variable may be modified by reducing the value of the adjustment variable. For example, the adjustment variable may be reduced in half in block 326-*j*.

In block 326-*k*, the current grayscale variable may be modified based on the adjustment variable. For example, as part of block 326-*k* the adjustment variable may be added to the current grayscale variable to generate an updated current grayscale variable. Flow may proceed from block 326-*k* to block 326-*a*.

In block 330 (see FIG. 12A), the previous grayscale variable may be provided as a representation of the fluid or fluid flow. The method 300 may end following block 330.

While some of the parameters described above in conjunction with the method 300 were described in terms of volume, the parameters may be expressed in other terms (potentially in lieu of expressing the parameters in terms of volume). For example, at least some of the parameters may analogously be expressed in terms of mass via one or more factors that may be used to convert between volume and mass, as described further below.

Figure 13:
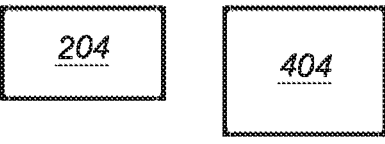
FIG. 13 illustrates a fixture in accordance with aspects of this disclosure.

In some embodiments, a calibration may be performed in connection with the fixture 202. For example, and referring to FIG. 13, a fixture 402 (which may correspond to the fixture 202 of FIG. 11) may be configured to retain the sample 204 and a reference sample 404 (which may correspond to the reference sample 204 of FIG. 11: in FIG. 13, details of the retaining mechanism 206, the bore 208, and the wrapper 212 are omitted, with the understanding that the same or analogous components may be applied to the sample 204 and/or the reference sample 404 in the fixture 402 of FIG. 13). The reference sample 404 may be used to calibrate the grayscale value due to the fluid in the reference sample 404 being the same as that being introduced into the sample 204, as well as the mass or volume of the fluid being predetermined/known.

If the reference sample 404 is placed/located out of plane with respect to the sample 204, the likelihood of any other materials with the same grayscale value appearing in-plane with the reference sample 404 is sufficiently low in relation to any potential impact on accuracy (aside from an insignificant amount of noise that may be present). Therefore, if a correct grayscale value is chosen, volume statistics calculated between the planes containing the reference sample 404 may prove accurate.

Figure 14:
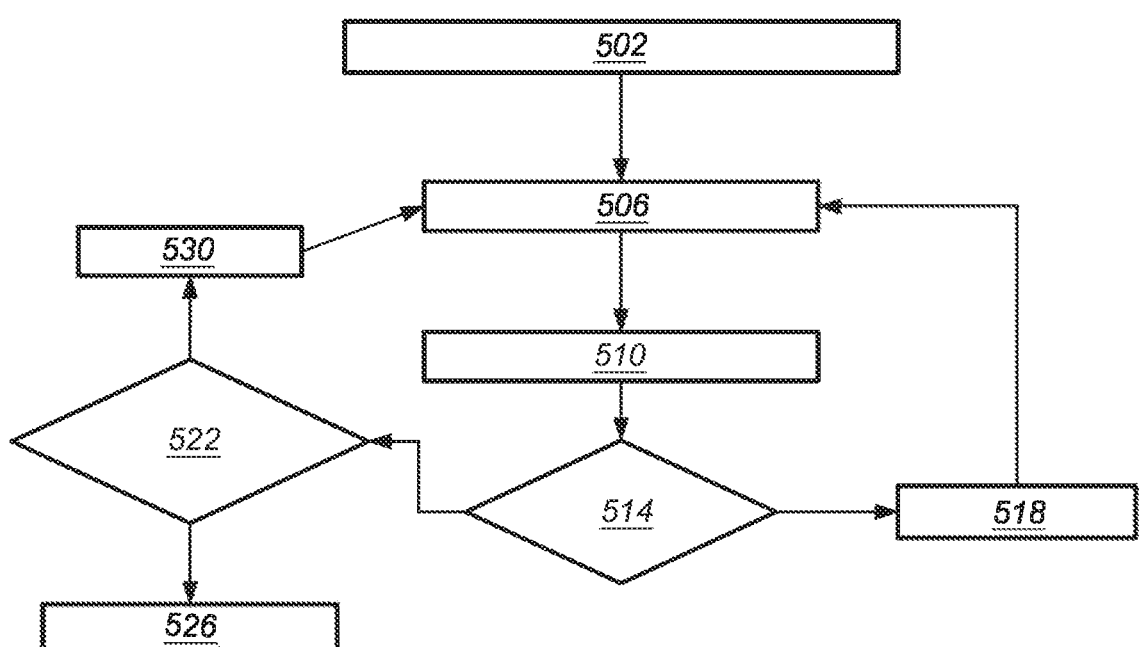
FIG. 14 illustrates a flow chart of an exemplary method for representing a fluid or fluid flow associated with a sample based on the use of a reference.

Referring now to FIG. 14, a flow chart of a method 500 is shown. The method 500 may be executed to obtain a grayscale value representative of a fluid or fluid flow. The method 500 may be similar to, or incorporate aspects of, the method 300 described above. Aspects of the method 300 and the method 500 may be combined with one another in some embodiments. The method 500 may be executed in conjunction with the system 200 of FIG. 11, or a portion thereof. The method 500 may be executed in conjunction with the fixture 402 of FIG. 13.

In block 502, a data set/reconstruction (e.g., block 302), an estimate of a grayscale value (e.g., block 306), a location of a reference sample (e.g., the sample 404), and a specification of the actual mass or volume of the reference sample may be obtained. The location of the reference sample may be specified in terms of one or more planes (e.g., two planes). As part of block 502, an adjustment variable may be obtained/set, similar to block 322. Similarly, a current grayscale variable may be obtained/set, similar to block 318.

In block 506, masses or volumes may be calculated for the data set of block 502 based on the current grayscale variable where the reference sample is located. As part of block 506, a volume may be converted to a mass by multiplying the volume by the fluid's density. Block 506 may be analogous, or similar, to blocks 326-*a* and 326-*b*. As part of block 506, one or more filtration or averaging techniques (e.g., root-mean-square (RMS)) may be applied.

In block 510, an error may be calculated as a difference between the (average) mass/volume calculated in block 506 and the actual reference sample mass/volume obtained in block 502. Block 510 may be analogous, or similar, to block 326-*c*.

In block 514, the error calculated in block 510 may be compared to a threshold (e.g., the error calculated in block 510 during a previous iteration of the method 500, which may be stored in a "previous error" variable). If the error of block 510 is less than the threshold, flow may proceed from block 514 to block 518. Otherwise, flow may proceed from block 514 to block 522. Block 514 may be analogous, or similar, to block 326-*d*.

In block 518, the current grayscale variable may be stored/saved (into a previous grayscale variable) and then the current grayscale variable may be modified using the adjustment variable. Block 518 may be analogous, or similar, to blocks 326-*e* and 326-*g*. Flow may proceed from block 518 to block 506.

In block 522, a determination may be made whether the adjustment variable is less than a (second) threshold. Block 522 may be analogous, or similar, to block 326-*f*. If the adjustment variable is less than the threshold, flow may proceed from block 522 to block 526 (and any iteration in connection with the blocks 506-526 and 530 may be ended in a manner similar to block 326-*h*). Otherwise, flow may proceed from block 522 to block 530.

In block 530, the grayscale value may be stored/saved (into the previous grayscale variable) and then the current grayscale variable may be modified on the basis of a modified value for the adjustment variable. Block 530 may be analogous, or similar, to blocks 326-*i*, 326-*j*, and 326-*k*. Flow may proceed from block 530 to block 506.

In block 526, the saved/stored (e.g., previous) grayscale value (as reflected in the previous grayscale variable) may be selected to represent the fluid or fluid flow. Block 526 may be analogous, or similar, to block 330.

As described herein, the methodological acts and processes may be tied to particular machines or apparatuses. For example, one or more computers may include one or more processors and memory storing instructions, that when executed, perform the methodological acts and processes described herein. Furthermore, the methodological acts and processes described herein may perform a variety of functions including transforming an article (e.g., a data set) into a different state or thing (e.g., a grayscale value representative of a fluid flow in a sample). In some embodiments, the transformation may take place in accordance with a predefined algorithm or formula.

While some of the examples described herein related to personal care products, one skilled in the art would appreciate that aspects of the disclosure may be applied in connection with other types of samples.

Technical effects and benefits of this disclosure include an ability to accurately and quickly characterize a fluid flow applied to a sample as the fluid enters and flows through the sample. This characterization may be made available on a substantially real-time basis, providing insight into the progression of the fluid through the sample.

Aspects of the disclosure have been described in terms of illustrative embodiments thereof. Numerous other embodiments, modifications, and variations within the scope and spirit of the appended claims will occur to persons of ordinary skill in the art from a review of this disclosure. For example, one of ordinary skill in the art will appreciate that the steps described in conjunction with the illustrative figures may be performed in other than the recited order, and that one or more steps illustrated may be optional in accordance with aspects of the disclosure. One or more features described in connection with a first embodiment may be combined with one or more features of one or more additional embodiments.

What is claimed is:

1. A method for measuring fluid absorption and retention of a personal hygiene article, comprising the steps of:
   obtaining a reference sample of the personal hygiene article;
   obtaining a mass of the reference sample;
   inputting the mass of the reference sample into a computer;

placing the reference sample adjacent or within a fixture, the fixture comprising a radiotransparent material;
   placing a line proximal to the reference sample such that the line is in fluid communication with the reference sample;
   positioning the reference sample and the fixture proximal to an imaging device such that the imaging device is capable of generating one or more images;
   inputting into the computer a flow rate for a fluid to be pumped through the line, the computer being in communication with a pump operatively connected to a fluid source and to the line;
   inputting into the computer a command to obtain one or more images of the reference sample when the fluid is pumped from the fluid source through the line and to the reference sample, the computer being in communication with the imaging device;
   inputting into the computer a command to commence the pump at the flow rate;
   acquiring one or more images from an imaging device;
   obtaining one or more data sets from the one or more images; and
   generating an estimate for a final grayscale value representative of a fluid flow by adding up a volume of each of the one or more data sets;
   wherein a reference value for a fluid flow is provided; and
   wherein a grayscale value representative of the reference value for the fluid flow is estimated.

2. The method of claim 1, wherein the computer is configured to coordinate the imaging device and the pump.

3. The method of claim 1, wherein the computer is further configured to perform one or more methodological acts.

4. The method of claim 1, wherein a theoretical flow rate based on the grayscale value and the reference value for the fluid flow is obtained.

5. The method of claim 4, wherein a previous grayscale variable has a previous grayscale value.

6. The method of claim 5, wherein a current grayscale variable has a current grayscale value that set to estimate the current grayscale value.

7. The method of claim 6, wherein the volume of each of the one or more data sets based on the current grayscale variable is calculated.

* * * * *